(12) United States Patent
Harrison et al.

(10) Patent No.: US 10,786,021 B2
(45) Date of Patent: Sep. 29, 2020

(54) APPARATUS AND METHOD FOR DONNING HYGIENIC GLOVES

(71) Applicant: HYGIENEXT, LLC, Chicago, IL (US)

(72) Inventors: Martin W. Harrison, Chicago, IL (US); Steve B. Kalish, Highland Park, IL (US)

(73) Assignee: Hygienext, LLC, Chicago, IL (US)

( * ) Notice: Subject to any disclaimer, the term of this patent is extended or adjusted under 35 U.S.C. 154(b) by 0 days.

(21) Appl. No.: 15/754,380

(22) PCT Filed: Jul. 24, 2017

(86) PCT No.: PCT/US2017/043496
§ 371 (c)(1),
(2) Date: Feb. 22, 2018

(87) PCT Pub. No.: WO2019/022703
PCT Pub. Date: Jan. 31, 2019

(65) Prior Publication Data
US 2020/0138130 A1    May 7, 2020

(51) Int. Cl.
*A61B 42/10* (2016.01)
*A41D 19/00* (2006.01)
(Continued)

(52) U.S. Cl.
CPC .......... *A41D 19/0068* (2013.01); *A61B 42/10* (2016.02); *A61B 42/40* (2016.02);
(Continued)

(58) Field of Classification Search
None
See application file for complete search history.

(56) References Cited

U.S. PATENT DOCUMENTS

| 429,890 A | 6/1890 | Crispell |
| 882,312 A | 3/1908 | Hoefftcke |

(Continued)

FOREIGN PATENT DOCUMENTS

| AU | 2004237794 | 6/2006 |
| DE | 4125037 | 2/1993 |

(Continued)

*Primary Examiner* — Gene O Crawford
*Assistant Examiner* — Ayodeji T Ojofeitimi
(74) *Attorney, Agent, or Firm* — Greer, Burns & Crain, Ltd.

(57) ABSTRACT

An apparatus for donning hygienic gloves comprising a stack of glove sheets, a box and a dispenser. The box contains the stack of glove sheets and the dispenser removably holds the box. Each glove sheet comprises a top and bottom layer sealed together at a hand-shaped seam that defines a glove and a frangibly attached remnant portion, the bottom layer being longer the top layer at a cuff of the glove, the cuff having a hand opening therein. The box has a removable flap, preferably including a hand-shaped portion on a front panel of the box. The dispenser includes an opening preferably including a hand-shaped portion on a front panel of the box. In a preferred embodiment, the hand-shaped seam, hand-shaped flap portion, and hand-shaped dispenser opening are configured to substantially match and align.

16 Claims, 9 Drawing Sheets

(51) Int. Cl.
    *A61B 42/40*         (2016.01)
    *A61B 42/50*         (2016.01)

(52) U.S. Cl.
    CPC .......... *A61B 42/50* (2016.02); *A41D 19/0003* (2013.01); *A41D 2400/44* (2013.01); *A41D 2400/72* (2013.01)

(56) References Cited

U.S. PATENT DOCUMENTS

| | | | |
|---|---|---|---|
| 1,938,685 A | 7/1931 | Breuls et al. | |
| 1,996,377 A | 10/1933 | Hinchen | |
| 3,067,001 A | 12/1962 | McCollum | |
| 3,237,821 A | 3/1966 | Hayne et al. | |
| 3,695,493 A | 10/1972 | Karr | |
| 4,002,276 A | 1/1977 | Poncy et al. | |
| 4,069,913 A | 1/1978 | Harrigan | |
| 4,155,494 A | 5/1979 | Poncy et al. | |
| 4,159,069 A | 6/1979 | Poncy et al. | |
| 4,228,935 A | 10/1980 | Madray | |
| 4,275,812 A | 6/1981 | Poncy et al. | |
| 4,889,266 A | 12/1989 | Wight | |
| 4,898,309 A | 2/1990 | Fischer | |
| 4,909,413 A | 3/1990 | McCutcheon | |
| 4,915,226 A | 4/1990 | Keenan | |
| 4,915,272 A | 4/1990 | Vlock | |
| 4,971,233 A | 11/1990 | Keenan | |
| D316,176 S | 4/1991 | Fischer | |
| 5,058,785 A | 10/1991 | Rich et al. | |
| 5,078,308 A | 1/1992 | Sullivan | |
| 5,868,290 A | 2/1999 | Green, Sr. et al. | |
| 5,921,434 A | 7/1999 | Hollander et al. | |
| 5,927,543 A | 7/1999 | DeJardin et al. | |
| 6,053,380 A | 4/2000 | Sherrod | |
| 6,193,117 B1 | 2/2001 | Poschelk | |
| D440,740 S | 4/2001 | Anctil | |
| 6,419,131 B1 | 7/2002 | Rix | |
| 6,427,883 B1 | 8/2002 | Esten | |
| 6,497,340 B2 | 12/2002 | Grinberg | |
| 6,554,168 B2 | 4/2003 | Stobart | |
| 6,832,708 B2 | 12/2004 | Sinai | |
| 6,932,253 B2 | 8/2005 | Sato | |
| 6,953,130 B2 | 10/2005 | Corbett | |
| 7,174,257 B2 | 2/2007 | Wright et al. | |
| 7,377,410 B1 | 5/2008 | Webb | |
| 7,527,181 B1 | 5/2009 | Sullivan | |
| 7,635,067 B1 | 12/2009 | Flynn | |
| 7,703,647 B2 | 4/2010 | Gochanour | |
| 7,805,772 B2 | 10/2010 | Williams | |
| 8,146,776 B2 | 4/2012 | Balkin et al. | |
| 8,220,675 B2 | 7/2012 | Rohard | |
| 8,533,868 B2 | 9/2013 | Bhalla | |
| 8,550,314 B2 | 10/2013 | Kelly et al. | |
| 8,960,493 B1 | 2/2015 | Dennison | |
| 9,078,647 B2 | 7/2015 | Dennison et al. | |
| 9,186,012 B2 | 11/2015 | Rogers | |
| D769,562 S | 10/2016 | Damaschke | |
| D771,892 S | 11/2016 | Damaschke | |
| 9,532,674 B2 | 1/2017 | Dennison et al. | |
| 9,668,601 B1 | 6/2017 | Rogers | |
| 2003/0094468 A1 | 5/2003 | Sinai | |
| 2004/0245268 A1 | 12/2004 | Grinberg | |
| 2005/0066413 A1 | 3/2005 | Mattesky | |
| 2005/0155133 A1 | 7/2005 | Sato | |
| 2006/0010563 A1 | 1/2006 | Michel et al. | |
| 2006/0049199 A1* | 3/2006 | West | A61B 42/40 221/26 |
| 2008/0110944 A1 | 5/2008 | Webb | |
| 2010/0037365 A1 | 2/2010 | Bhalla | |
| 2010/0147909 A1 | 6/2010 | Kelly et al. | |
| 2011/0283439 A1 | 11/2011 | Backhaus et al. | |
| 2016/0051330 A1* | 2/2016 | Cosentino, II | A61B 50/20 221/45 |

FOREIGN PATENT DOCUMENTS

| | | |
|---|---|---|
| EP | 0347606 | 12/1989 |
| EP | 2339945 | 4/2014 |
| JP | H05287601 | 11/1993 |
| JP | H06285083 | 10/1994 |
| JP | H10202 A | 1/1998 |
| JP | H10108870 A | 4/1998 |
| JP | 2002212817 | 7/2002 |
| WO | 1994018900 | 9/1994 |
| WO | 1998017133 | 4/1998 |
| WO | 200241718 | 5/2002 |
| WO | 2005013842 | 2/2005 |

\* cited by examiner

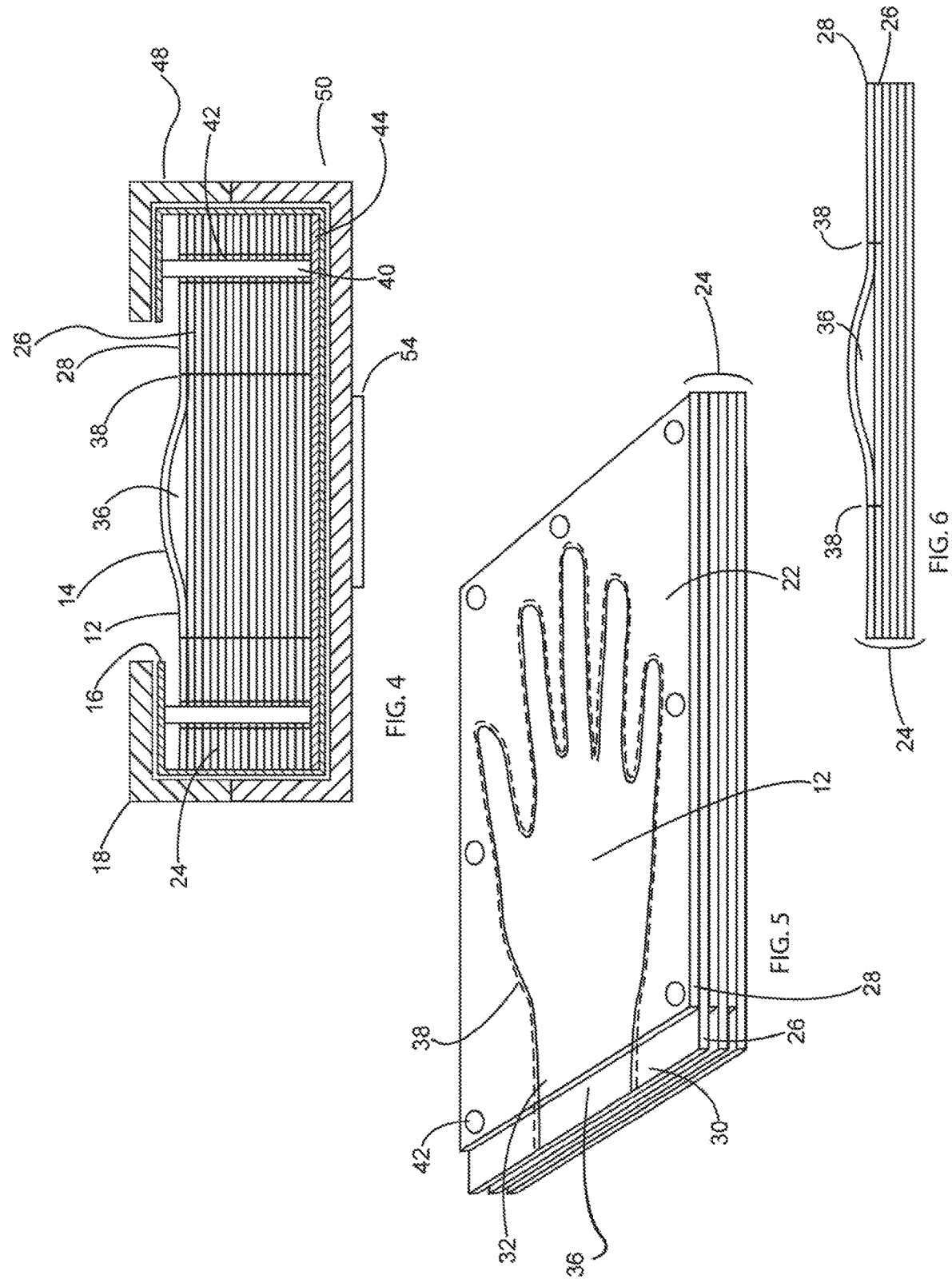

APPARATUS AND METHOD FOR DONNING HYGIENIC GLOVES

BACKGROUND OF THE INVENTION

A common problem in the use of hygienic gloves is donning a glove without contaminating it. Donning a glove can result in the glove becoming contaminated through contact with either of the users' hands. Ideally, users should don gloves with minimal, if any, contact with the outer surface of the glove to be used or with any other gloves contained in the packaging. An additional problem in the use of hygienic gloves is the lack of a mechanism or device to rapidly and easily don the glove using only a single hand.

The prior art solutions have focused on helping the user avoid contact with the rest of the glove while donning. However, these solutions do not allow for the single-handed donning of multiple gloves by multiple users in repeat succession, with minimal set up and while simultaneously avoiding contact with the outer surface of the glove. This problem has not been adequately addressed by others in the art.

OBJECTS OF THE INVENTION

The objects of the invention include one or more of the following:
  Providing an apparatus for rapidly and easily donning gloves using only a single hand,
  Providing a glove donning apparatus that protects gloves from contamination by minimizing exposure of the gloves prior to and during donning,
  Providing a cost-effective solution that can be utilized in wide variety of medical, food service and commercial applications,
  Providing a glove donning apparatus that does not require electrical or compressed air components, and
  Providing a glove donning apparatus that is easy to supply and maintain.

SUMMARY OF THE INVENTION

The present invention provides an apparatus and method for donning hygienic gloves that allows the user to quickly and with minimal effort, don both right and left gloves, one-handed, while minimizing the possibility of contamination. It also provides a low cost hygienic glove dispensing and donning apparatus that would have practical application in both the medical and food service industries as well as in general use.

The apparatus of the invention for donning hygienic gloves comprises a plurality of glove sheets bound together in a stack, a box or package containing the stack of glove sheets, and a dispenser for removably holding the box such that the box of gloves can be replaced when empty. Each glove sheet comprises a top layer and a bottom layer, the bottom layer being longer on a proximal side than the top layer thereby forming a tail. Each glove sheet comprises a bi-layered glove and a remnant portion, the glove being frangibly connected to the remnant portion, such that the glove can be easily torn away from the remnant portion by the user when donning a glove. The top and bottom layers of each sheet are sealed together in a hand-shaped seam to form the glove, the glove having a cuff and a hand opening therein on the proximal side of the glove sheet.

The box containing the stack of glove sheets protects the gloves from contamination. The box may include posts or other fasteners for securing the remnant portions of the glove sheets together. The sheets are also bonded or heat-sealed together within the remnant portion. In a preferred embodiment, the sheets include strategically positioned sealing points in the remnant portion of each sheet. The sealing points together maintain the integrity of the stack and facilitate clean separation from the remnant and removal from the stack.

The box includes a detachable flap aligned substantially with the glove portion of the glove sheets such that removal of the flap exposes a top one of the glove sheets. The detachable flap preferably has the overall configuration of a glove. More specifically, the detachable flap has a glove outline that corresponds to the gloves within the stack such that the remnant portions of the glove sheet are substantially covered by a portion of the front panel of the box that remains after the flap is detached.

The dispenser holds the box, the box being removable from the dispenser. The dispenser includes an opening on a front face configured to be substantially aligned with the detachable flap of the box. In the preferred embodiment, the peripheral margins of the opening in the dispenser matches and aligns with the outline of the removeable flap, which also matches and aligns with the outline of the gloves. A back panel of the dispenser preferably includes a wall mount, whereby the dispenser can be vertically mounted on a wall, preferably 4-5 feet above the floor. The dispenser may optionally be placed or mounted horizontally or may be mounted at an angle. A user dons a glove by extending and sliding his/her fingers over the tail portion of the bottom layer, under the top layer and into the hand opening. A simple inward and upward motion causes the glove to tear away from the remnant. Accordingly, the glove can be donned quickly and easily using only one hand, without making any contact with the exterior surface of the glove and without contacting the other gloves in the package. A single dispenser and stack can be used for either the right or left hand with a pronation and supination movement. However, a pair of dispensers can be provided for right and left gloves. In one embodiment, a single dispenser is provided with a one-size-fits-all glove. Other embodiments may include multiple dispensers with different size gloves. Preferably, the gloves sheets are stretchable polyethylene film. The box or package can be a plastic box or even a poly wrappers, but preferably is a cardboard box. In one embodiment, the box is a plastic wrapped cardboard box—the plastic wrap being removable before the box is inserted into the dispenser. The term "box" as used herein means any sort of box, bag or package the encloses and contains the stack of glove sheets. The dispenser can be made of any substantially rigid and durable material, such as molded plastic, aluminum or other metals. More preferred materials include one-piece molded acrylic and stainless steel.

The invention further includes a method of donning hygienic gloves that comprises the steps of providing a dispenser having a hand-shaped opening on a front panel and a box of gloves, the box having a hand-shaped detachable flap on a front panel, installing the box of gloves in the dispenser, and removing the flap from the front and bottom side of the box to expose an upper one of a stack of glove sheets in substantially hygienic condition. A person can easily don a glove by extending and sliding his/her fingers over a tail portion of a bottom layer of the glove, under a top layer and into a hand opening. A simple inward and upward motion causes the glove to fully don and tear away from the remnant portion and the other glove sheets in the stack. The method preferably includes a step of separating the top layer of the next glove from its bottom layer as the previous glove is torn away.

Further objects and advantages of the invention will be apparent from the drawings and the following detailed description of preferred embodiments.

BRIEF DESCRIPTION OF THE DRAWINGS

FIG. 4 is a cross sectional view of the first embodiment.

FIG. 5 is a perspective view of a stack of glove sheets of the first embodiment.

FIG. 6 is a proximal end view of the stack of glove sheets of the first embodiment.

DETAILED DESCRIPTION OF THE PREFERRED EMBODIMENTS

Figure 3:
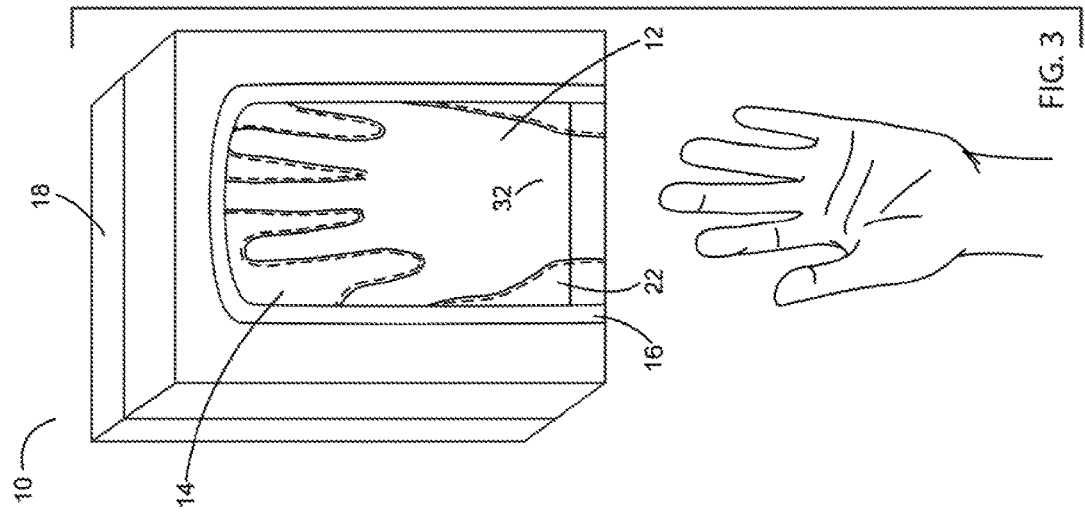
FIG. 3 is a perspective view of a left hand being inserted into a glove.
Figure 2:
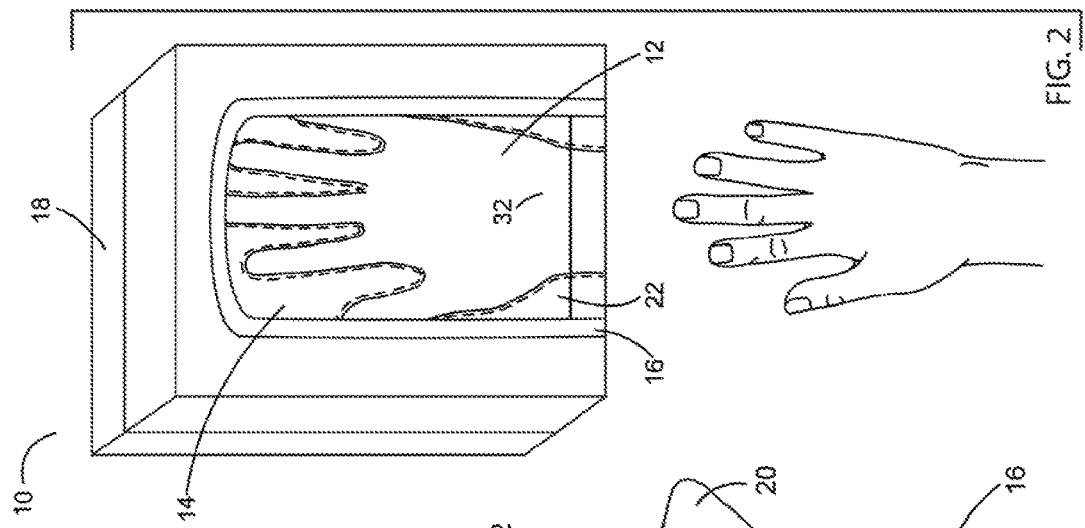
FIG. 2 is a perspective view of a right hand being inserted into a glove.
Figure 1:
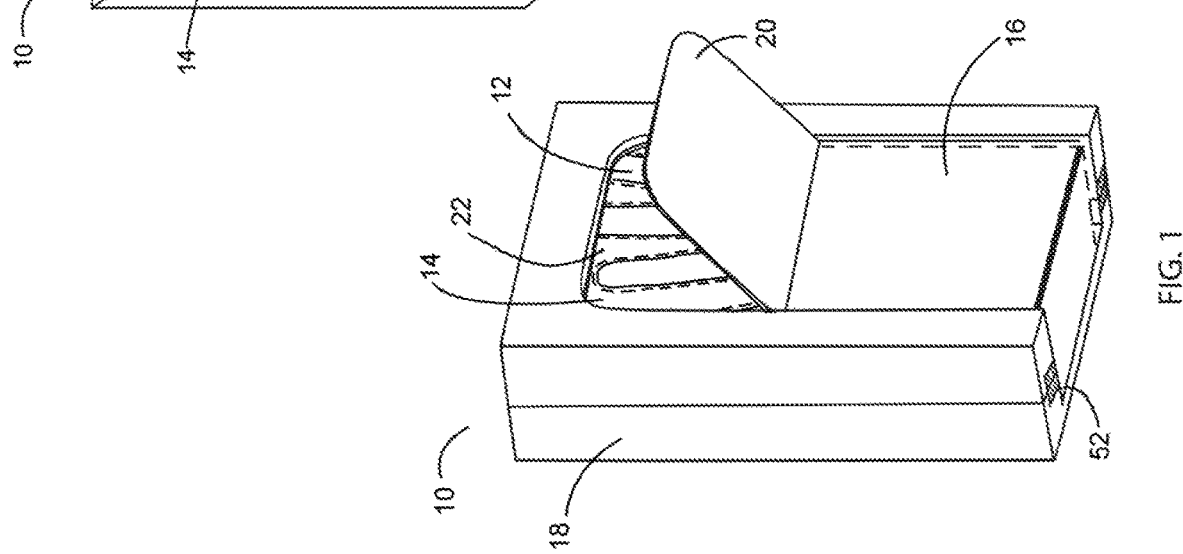
FIG. 1 is a perspective view of a first embodiment of a glove donning apparatus with a removable flap partially pulled away.

Referring now to FIGS. 1-3, a first embodiment of a glove donning apparatus 10 for dispensing disposable gloves 12 comprises a plurality of glove sheets 14 bundled together for stability and contained within a box or package 16. The package is removably held within a dispenser housing 18, which is preferably wall mounted. Alternatively, the dispenser can be mounted horizontally or at an angle. The dispenser can also be unmounted. Gloves 12 can be accessed by removing a flap 20 from the package 16, as shown in FIG. 1. A user can then slip either a left or right hand into a hand opening of the glove, as shown in FIGS. 2 and 3, and tear away a glove 12 leaving a remnant 22 of the glove sheet behind. Accordingly, users may quickly and easily don gloves using one hand without touching the exterior of the glove or any of the other gloves in the stack, thereby reducing the risk of contamination. A single dispenser can be used for both right and left hands as shown in FIGS. 2 and 3. Alternatively, right and left dispensers can be provided, the left-hand dispenser being a mirror image of the illustrated right hand dispenser. Also, two or more dispensers can be provided for different size gloves, if desired.

As shown in FIG. 4-5, the first embodiment of a glove donning apparatus 10 contains a stack 24 of glove sheets 14 which are preferably bound together and contained within package 16, which is in turn is removably held in dispenser 18. Each sheet 14 is rectangular in plan view and is slightly longer and wider than each glove 12. Glove sheet 14 can be formed by a conventional process from two layers of plastic film A bottom layer 26 is longer than the top layer 28 to form a tail portion 30. The glove 12 has a slightly elongated cuff 32 having a hand opening 36. The tail 30 at a proximal end 34 of the cuff facilitates ease of entry of the user's hand into the glove. A hand-shaped seam 38 is formed when the top and bottom layers of plastic are heated and pressed together, as per the conventional process that is well known in the art. The glove 12 is loosely or frangibly connected to the rest of the sheet as a result of the heat sealing process or alternatively with a line of perforations 39, whereby the glove can be easily torn away from the sheet leaving behind remnant 22. Preferably the frangible connection at the cuff is stronger than the frangible connection at the fingers. Thereby the glove will not tear away as the user inserts his or her hand, but once the hand is fully inserted, the user can easily tear the glove away beginning with the cuff and proceeding upwardly to the hand and fingers.

The layers 26 and 28 which comprise the glove sheet can be formed from plastic film fed off rolls. The glove is formed by heat-sealing the two layers 26 and 28 forming a seam 38 in the shape of a hand. The plastic film is preferably stretchable polyethylene or alternative materials, such as conventional polyethylene film, other polymers such as polyvinyl. A preferred embodiment is one size fits all ("OSFA") without a right/left orientation, but gloves could be offered in various sizes and/or in separate right and left configurations. Antimicrobial additives and/or lubricating substances to aid in donning could be applied between the top and bottom sheets.

Alternatively, to the above, the gloves could be made from a material like nitrile or latex rather than polyethylene film. In this embodiment, the gloves may not be made from two "welded" layers, but rather by a conventional dipping process. In that case, the gloves would be removably attached to the substrate remnant.

Although not required, an optional means may be provided to separate the top and bottom glove layers to aid in the donning of gloves. As schematically shown in FIG. 6, as each glove 12 is torn away from the stack 24, the bottom layer 26 of the removed glove pulls gently on the top layer 28 of the glove sheet below it in the area of cuff 32 to separate the top and bottom layers creating a partial hand opening 36 for the next glove to be dispensed. The partial hand opening 36 allows the next user to easily slip his or her hand into the next glove 12 without touching and potentially contaminating any other portion of the glove 12. This effect can be achieved in a variety of ways. In one embodiment, a weak adhesive is applied between the glove sheets in the cuff area. Thereby, the bottom layer of a first glove sheet is lightly adhered to the top layer of the underlying second glove sheet. Removal of the first glove 12 causes the top layer 28 of second glove to separate from its bottom layer 26. In another embodiment, the mechanical energy of removing each glove 12 provides a mechanical advantage by friction to partially open the next glove 12. In yet another embodiment the successive gloves sheets 14 can be connected by folds or the like to allow for partial opening of the cuff 32 of the successive glove, i.e., like in a box of tissues.

Electromechanical and/or pneumatic devices are also options for separating the layers, but are not preferred as they add cost and complexity. As indicated above, separation means is optional because a user can simply slide his/her hand into the glove opening without any separation means.

As the glove sheets 14 are cut from the roll (after glove forming), they are stacked and packaged one on top of another with the glove portions being aligned. Packaging is such that the form of the sheet (and stack of sheets 24) is maintained as flat and with edges aligned evenly and in sufficient number, e.g., 50 sheet per stack, to be determined to completely fill one box or package 16. The stack of glove sheets 24 are bundled, stabilized and/or secured together. The stack of gloves may be bonded or glued or otherwise fixed together, in the remnant portion, to aid in this stabilization.

Figure 7:
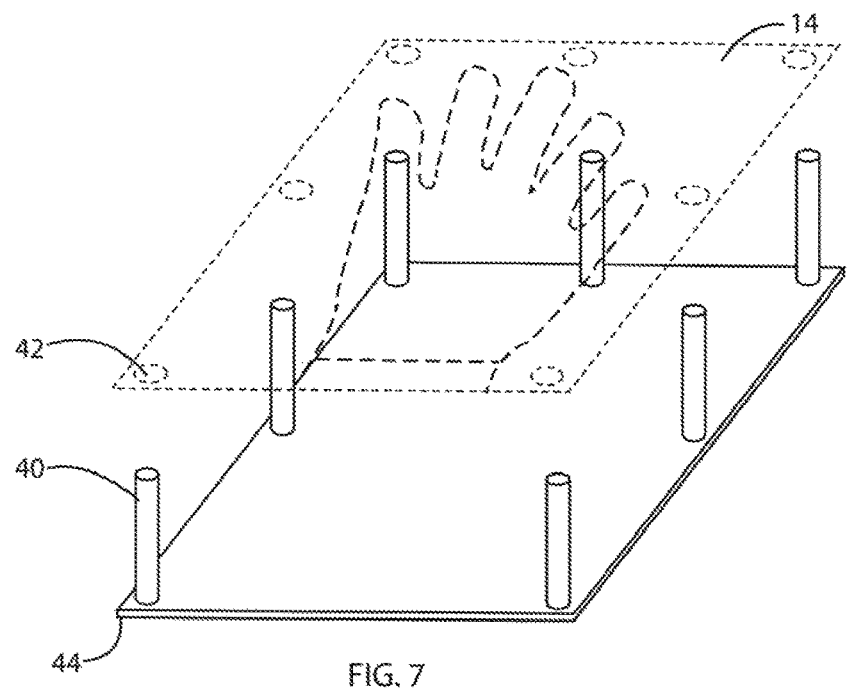
FIG. 7 is a perspective view of a binding and/or stabilizing device for the stack of glove sheets of the first embodiment.

Referring to FIGS. 4 and 7, in the first embodiment, the stack 24 of glove sheets 14 are secured by a plurality of posts 40 which extend through corresponding holes 42 located in the remnant portion 22 of glove sheets 14. Although seven posts are shown, other embodiments may have as few as two posts. The posts 40 extend perpendicularly from a back template 44 that is contained within box 16. Alternatively, the back template 44 can constitute the rear panel of the package. The posts extend outwardly from the back template through an optional front template 45 thereby securing the stack 24 between the back and front templates. The back template is preferably fixed to the posts. The front template can be, but need not be, fixed to the posts.

Front template 45 is sized so that the outer periphery fits snugly within the box, and includes a central opening for removal of gloves. The opening is preferably hand-shaped to match and align with the seam 38. The front template guides the user where to insert their hand to don a glove, helps hold the remnant portions while a glove is being removed, and aids in the clean tear-away of the glove from the remnant and stack.

In an alternative embodiment, the posts 40 are mounted on the dispenser 18 as discussed below and the package 16 and glove sheets 14 are provided with corresponding holes 42. In yet another alternate embodiment the posts extend through the back panel and/or front panel of the package with or without additional back or front templates.

The posts 40 and templates 44 and 45 can be fabricated from any suitable material. The posts can be plastic, metal or wood. The templates can be plastic, cork, cardboard, metal or wood. Preferably the posts 40 and templates 44 and 45 are molded plastic. The posts 40 and front template 45 assure that when a user pulls away, glove 12 cleanly separates, the remnant 22 stays behind in the box 16, and the remaining glove sheets 14 are not dislodged or twisted, i.e., the integrity of the stack 24 is secured.

There are numerous alternative means by which the stack of glove sheets can be bundled, stabilized and/or secured within box 16. Preferably the sheets within the sack are heat-sealed together at certain points within the remnant portion to maintain the integrity and shape of the stack as gloves are donned. In an alternative embodiment, the remnant portions 22 of successive glove sheets 14 can be secured together by adhesive, friction welding, rivets, pins, ribbons, other fasteners, or simply under pressure provided in the packaging. In yet another alternative embodiment each glove sheet 14 can be attached on their peripheral edges to other sheets in the stack, and/or to the interior sides of the package or box 16. These and other bundling means will be apparent to those skilled in the art and may involve a combination of one or more of these methods.

Figure 8:
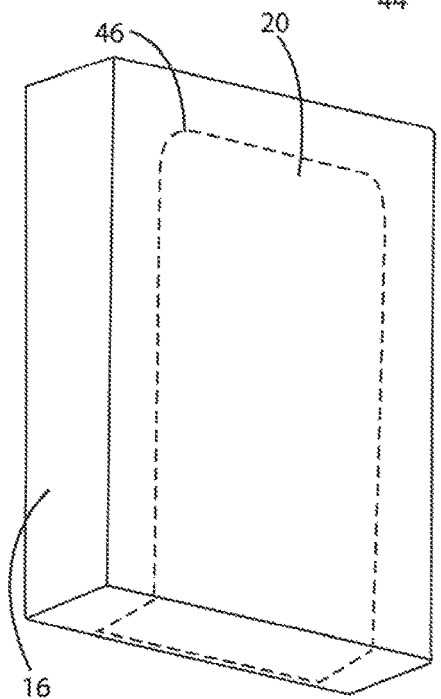
FIG. 8 is a perspective view of a box or package of glove sheets of the first embodiment.
Figure 9:
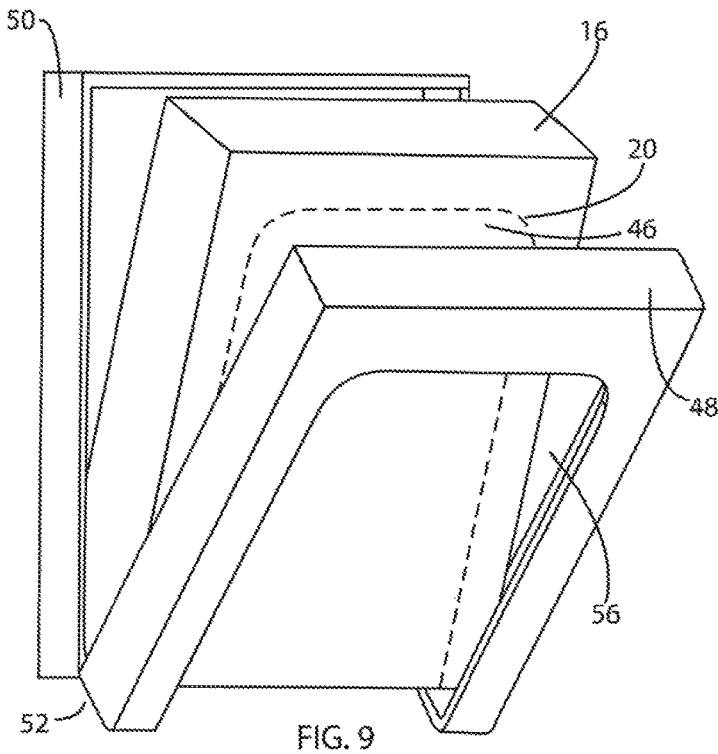
FIG. 9 is a perspective view showing installation of the box within the dispenser of the first embodiment.
Figure 10:
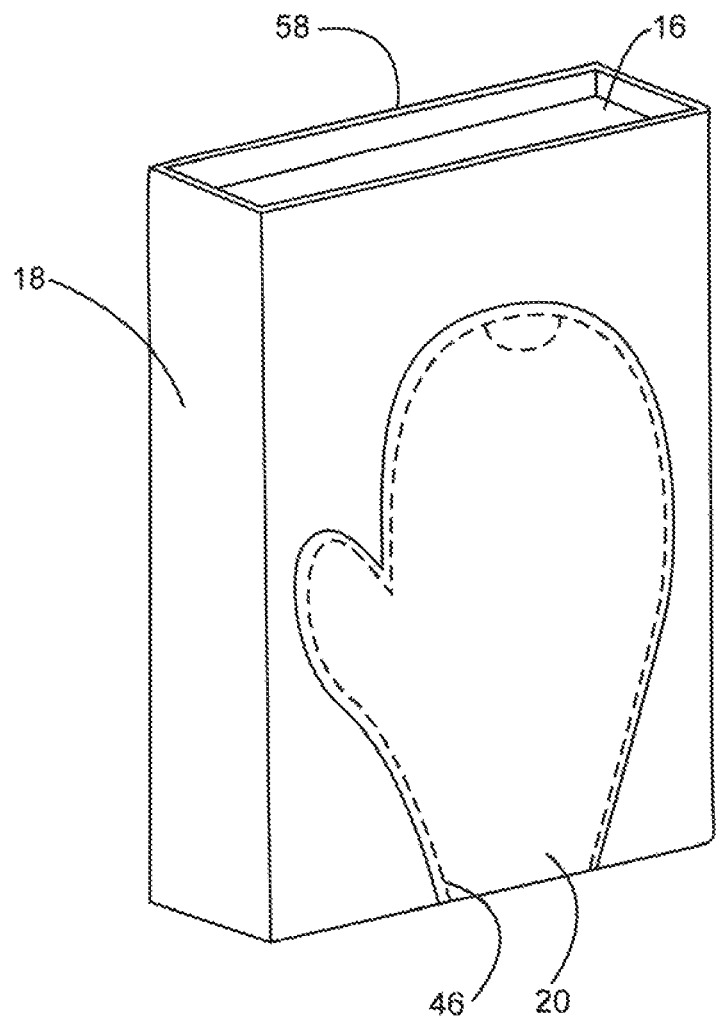
FIG. 10 is a perspective view of second and more preferred dispenser embodiment.

FIGS. 8 and 9 are perspective views of the box 16 and the dispenser 18. The box 16 includes a line of perforations 46 defining a removable flap on the front panel and one end panel of the box. The line of perforations 46 can be generally rectangular as shown in FIG. 1 or more preferably glove shaped as shown in FIG. 10. Other shapes are contemplated. The flap 20 covers an area corresponding to the glove 12 and the proximal end 34 of the glove sheets. The box front flap and the front panel of the dispenser preferably more precisely outline and are slightly larger than the actual gloves. Removing the flap 20 exposes the glove stack 24 within the box 16. The box 16 can be fabricated from any suitable material, e.g., a cardboard.

The dispenser 18 can be constructed of sturdy but thin material, either plastic, such as molded acrylic, or metal, such as aluminum or stainless steel. One embodiment of the dispenser 18 comprises a front portion 48 and a rear portion 50 which are attached at the proximal end by a hinge 52. A wall mount 54 is attached to a rear portion 50 of the dispenser. In this configuration, the dispenser 18 can be vertically mounted to a wall, preferably 4-5 feet above the floor. Alternatively, the dispenser can rest flat on a surface such as a desk or counter. When a box 16 of gloves 12 is exhausted, the front portion 48 can be pivoted away from the wall mounted rear portion 50. The empty box can then be removed, a fresh box inserted, and the front portion 48 closed again.

Alternatively, as shown in FIG. 10, the dispenser 18 can be a one-piece construction with top or end opening 58 or door from which a depleted box can be removed and a new box can be inserted. The opening 58 may include a door, latch or other device to secure the box within the dispenser and restrain shifting movement of the box as gloves are donned.

The dispenser 18 has an opening 56 corresponding generally to but slightly larger than the removable flap 20 of the box. Despite the opening, the dispenser has sufficient structure in front of the dispenser 18 at the perimeter and overlying the remnant portion of the gloves, to firmly secure the box 16 in place. Thereby, a box 16 can be installed opened or unopened in the dispenser 18 and then the flap 20 removed either before or more preferably after installation. Removing the flap after installation in the dispenser reduces the risk of contamination and helps maintain the hygienic condition of the gloves. In the wall-mounted, vertical orientation, at approximately 4-5 feet height, the opened package 16 present gloves 12 which can be easily donned by either hand by after using a lateral rotation of the hand (pronation or supination) to align with the glove, sliding the hand up between the two layers 26, 28 of one glove 12 and pulling (tearing) the glove 12 away from the stack 24 and dispenser 18.

In an alternate embodiment, posts 40 can be molded with or mounted to the rear panel of the dispenser rather than be part of the packaging process. In this embodiment, the package 16 and sheets 14 are provided with mating through holes 42. Accordingly, the package 16 is inserted onto the posts 40 that extend through the package 16 and the stack 24 of glove sheets 14, and thereby stabilize the glove sheets 14. The advantage of this alternative embodiment is that posts 40 are reused rather than thrown away with each empty package 16, thereby reducing costs.

Figure 11:
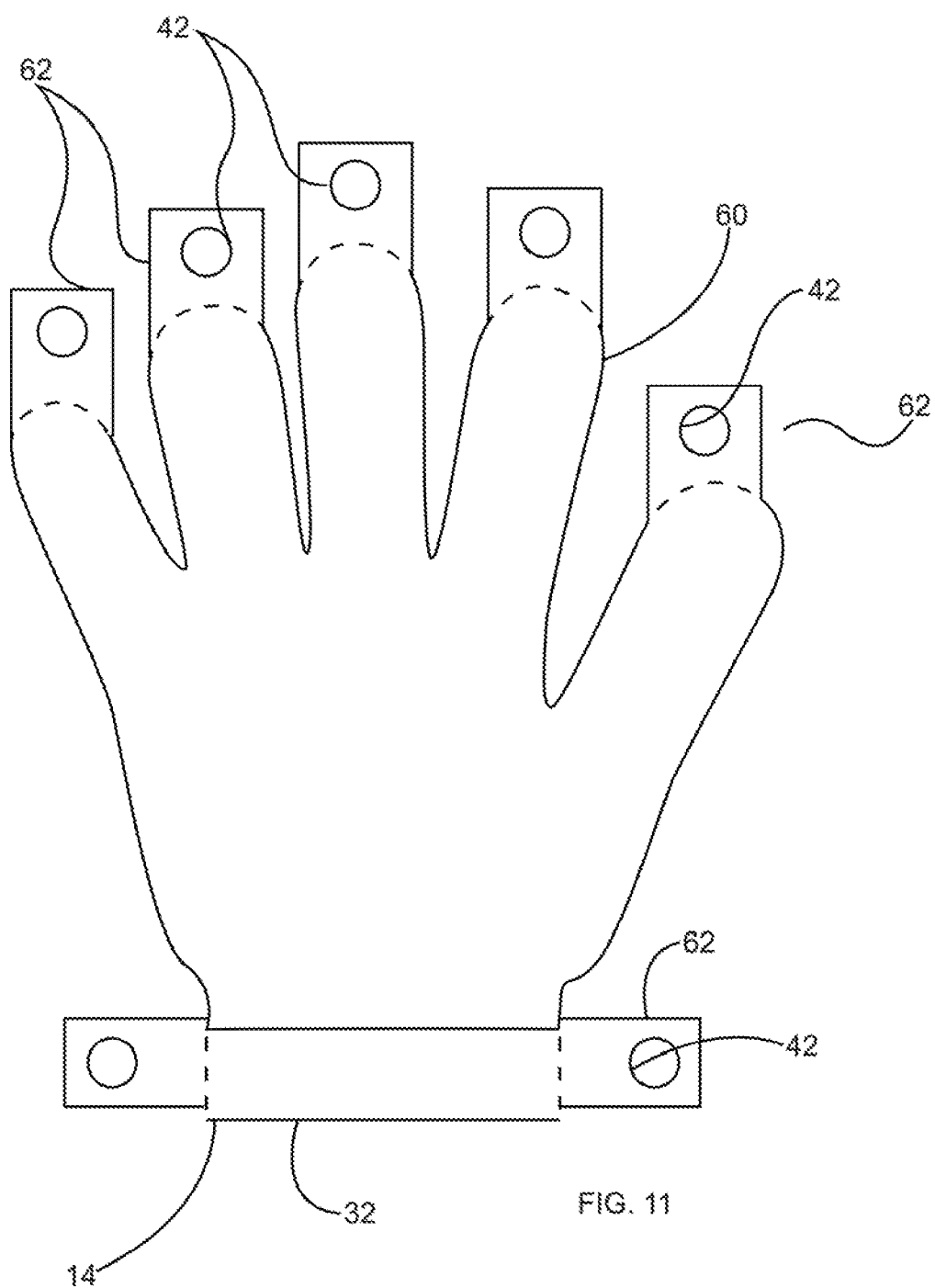
FIG. 11 is a plan view of an alternative glove sheet embodiment.

An alternative embodiment of a glove sheet 60 is shown in FIG. 11. The remnant portion of the sheet comprises two or more tabs 62 distal to respective fingers and a pair of tabs 62 lateral to either side of the bottom of the cuff 32. Preferably there is a tab securing each finger and the thumb as shown. The tabs are frangibly attached to the glove at these points. Additionally, the tabs have holes 42 for receiving aligned posts (not shown). The method for donning of the gloves and separation from the remnant portion remains essentially the same as in the first embodiment.

Figure 12:
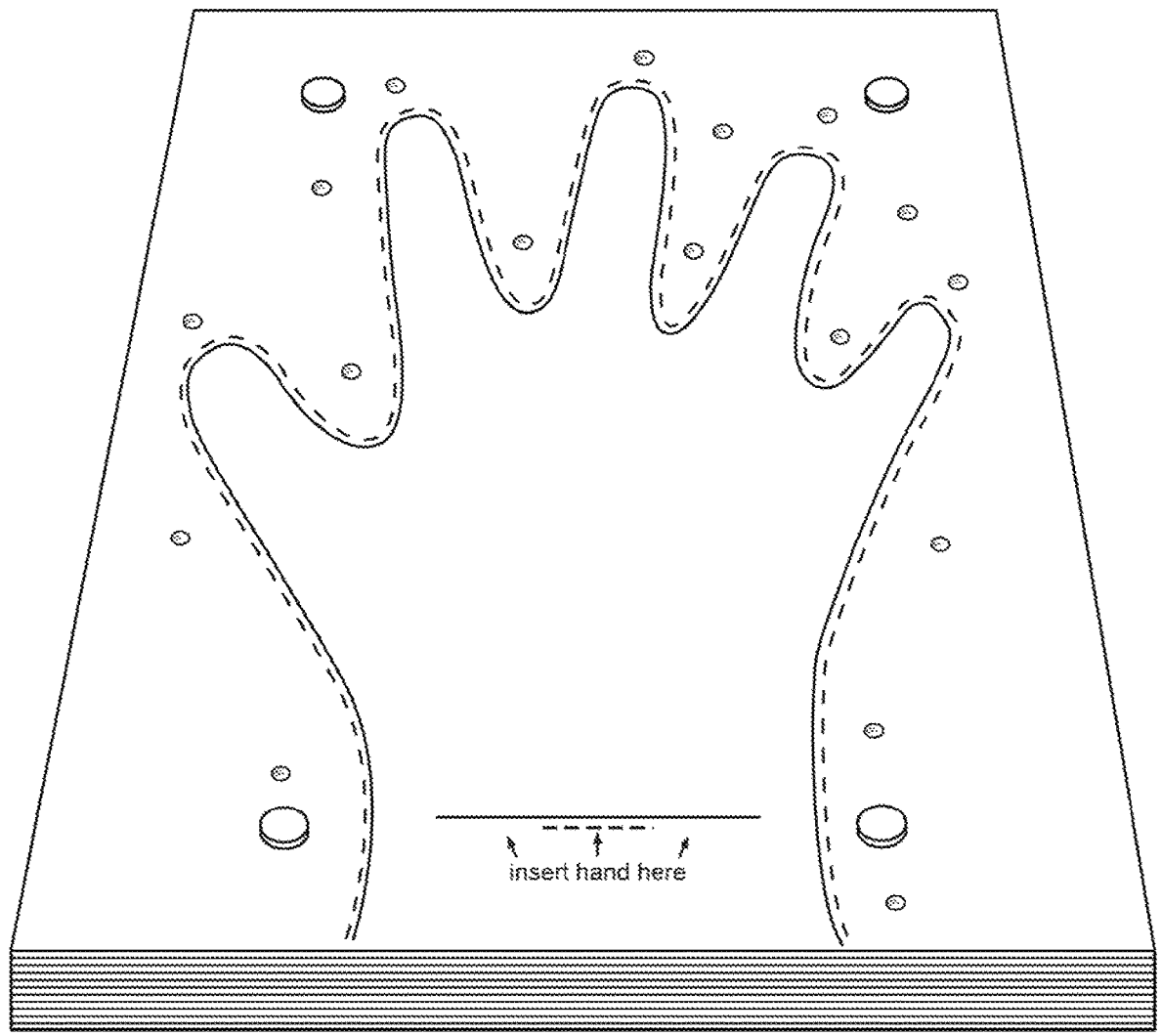
FIG. 12 is top and bottom end perspective view of a stack or bundle of gloves in second embodiment of the invention.

FIGS. 12-15 illustrate a second and more preferred embodiment of the apparatus. FIG. 12 shows a bundle or stack 24 of glove sheets 14. Each glove sheet 14 includes multiple strategically located sealing points 64 in the remnant 22. The bi-layers of sheets are bonded together at these multiple strategic places by heat sealing techniques. Any sealing or bonding technique can be used, such as ultrasonic or linear vibration welding. The sealing points help maintain the integrity of the remnants and facilitate clean removal of gloves 12. Additional anchors are provided by posts 40 securing the stack of gloves to the disposable box 16 or to a disposable back template 44 provided within each box of gloves. The illustrated embodiment uses four posts, one on each side of the cuff 32 at the bottom and one on each side near the top, at about the width of the thumb and 5th finger. Although four posts are shown, other embodiments may have as few as two posts, i.e., the pair of posts adjacent the cuff. The second embodiment does not include a front template.

Figure 13:
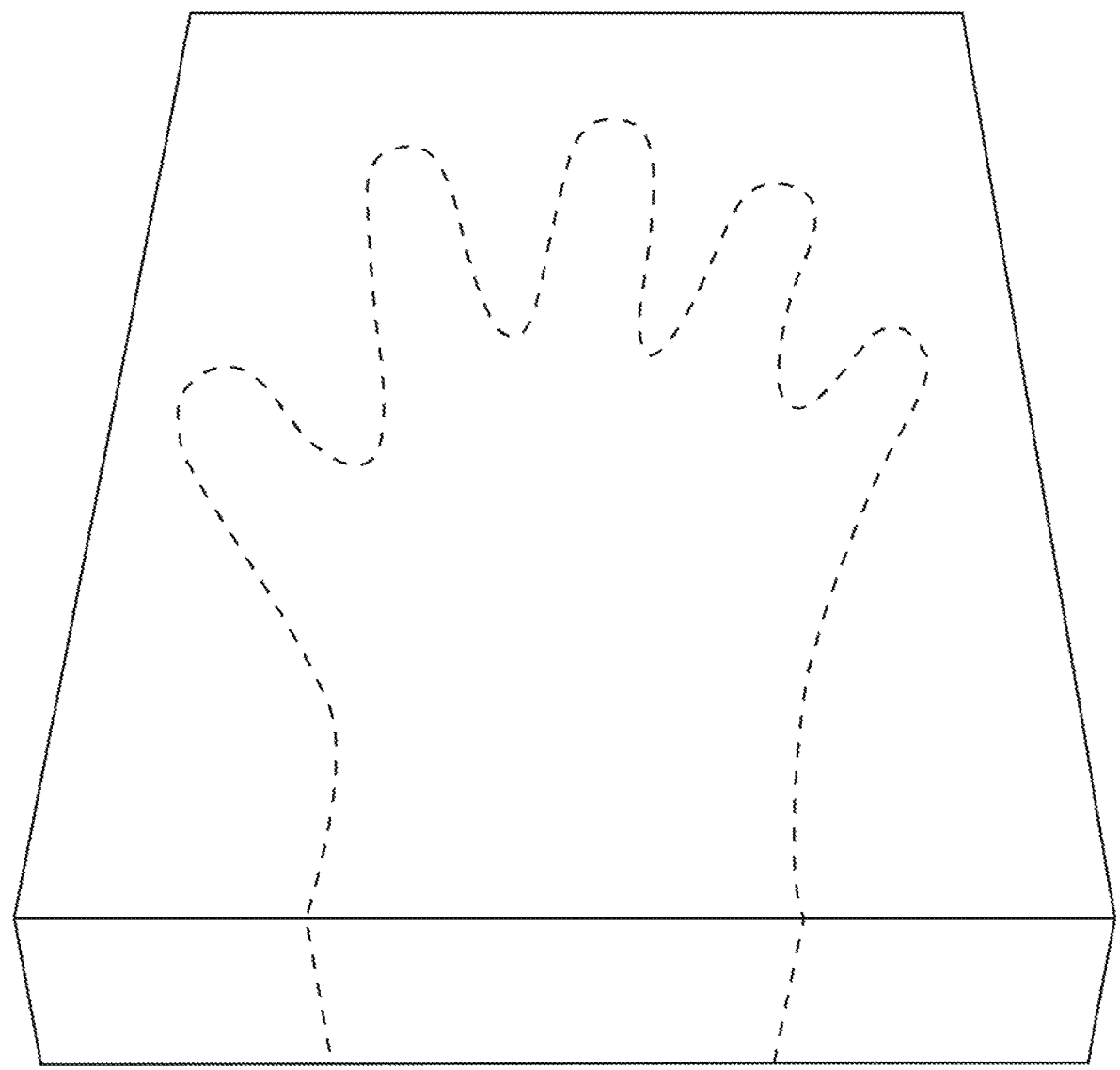
FIG. 13 is top and bottom end perspective view of a box or package of the second embodiment containing the stack of glove sheets shown in FIG. 12.

FIG. 13 shows a top view of a box 16 with a removable flap 20 defined by perforation line 46 on the front panel 15 and end panel 17. The flap is configured in a hand-shape that substantially matches and aligns with the outline of the glove 12 and seam line 38 in the stack 24. End panel 17 is adjacent the proximal end of the stack of gloves. Perforation line 46 on end panel 17 may extend fully to the back panel or partly to form a lip as illustrated. Accordingly, when the flap 20 is removed a top glove and the proximal end of the glove stack is exposed.

Figure 14:
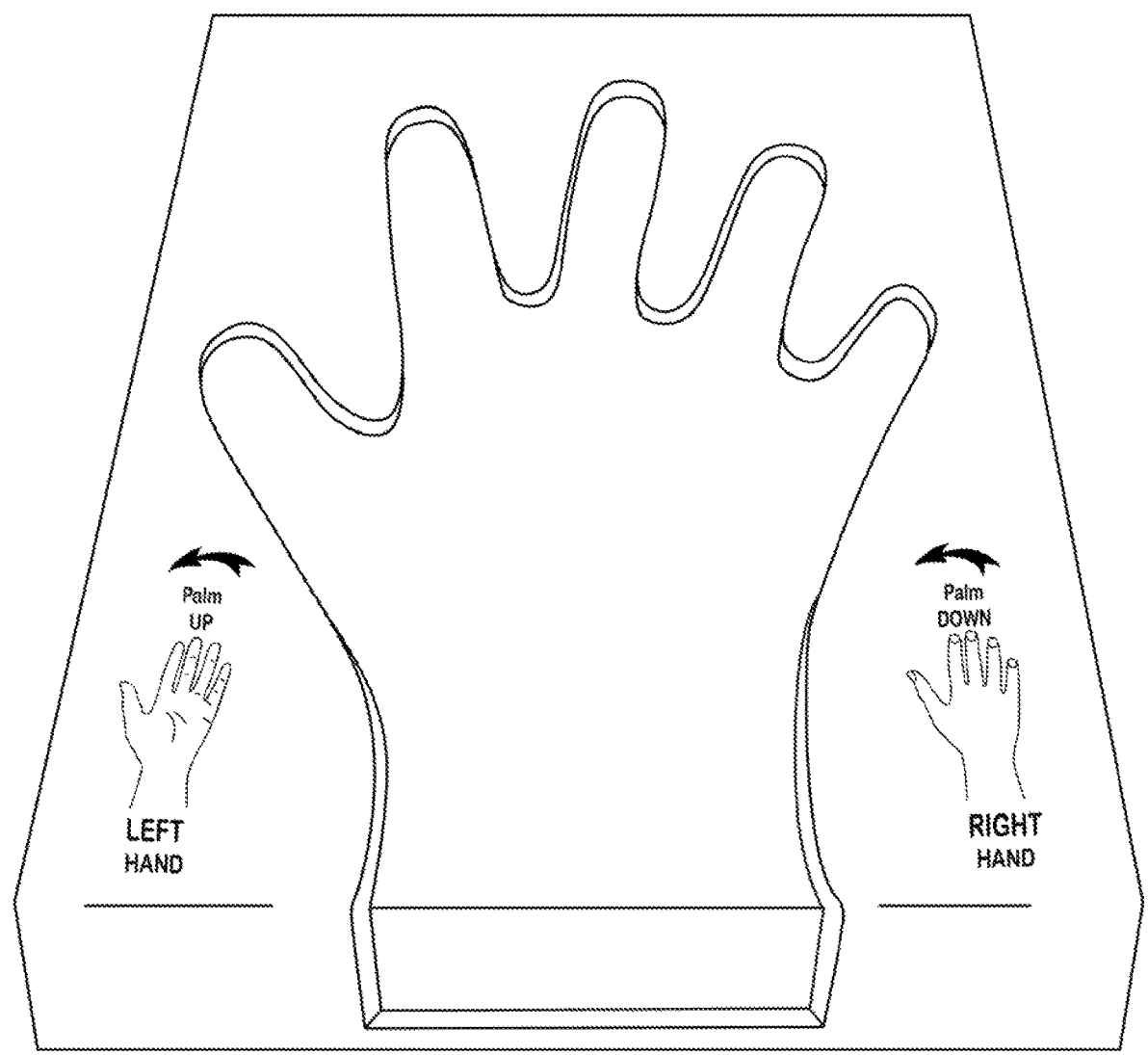
FIG. 14 is top and bottom end perspective view of a dispenser of the second embodiment containing the box of FIG. 13.
Figure 15:
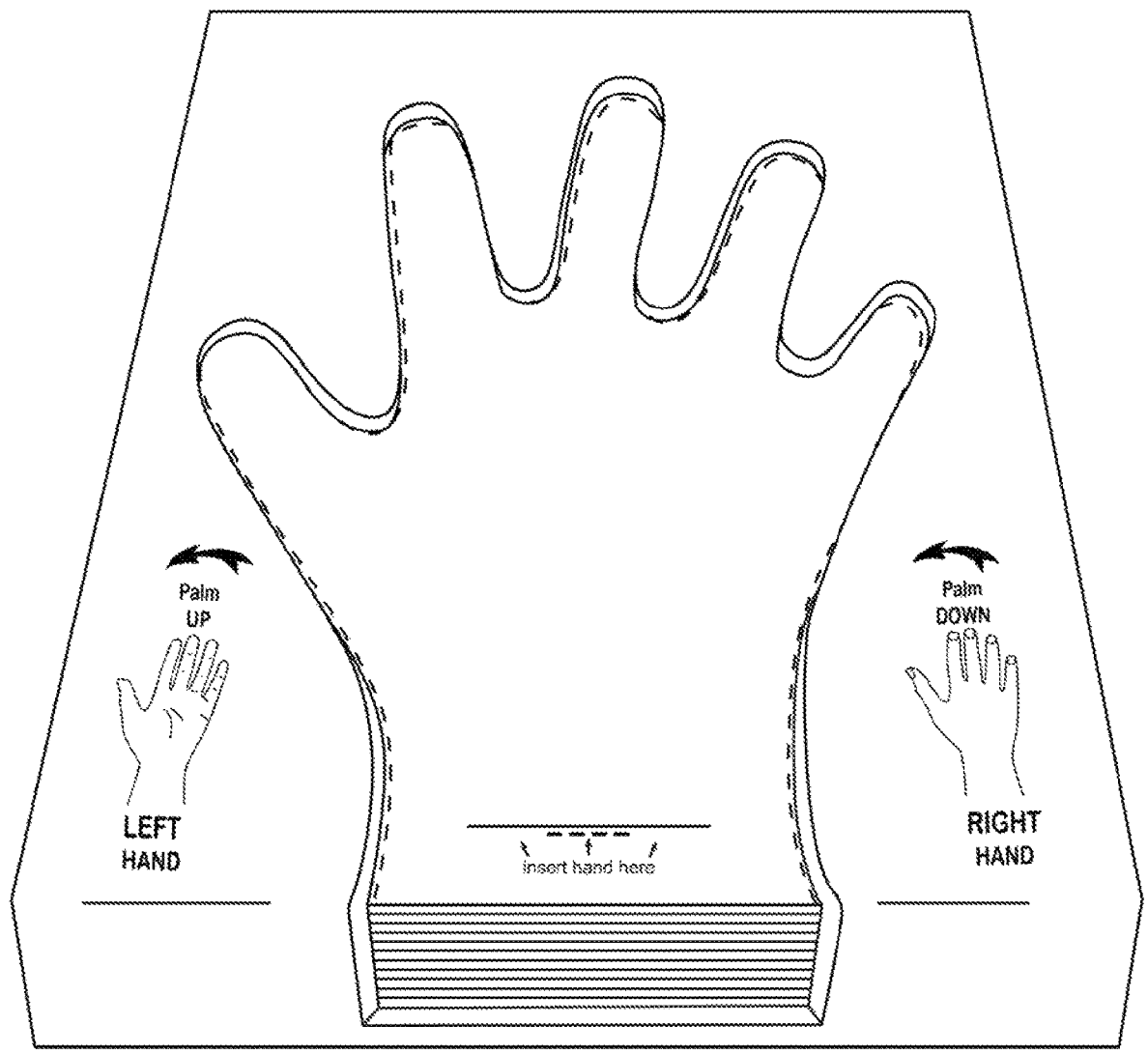
FIG. 15 is top and bottom end perspective view of the dispenser of the second embodiment containing the box with the flap removed revealing the stack of glove sheets.

FIG. 14 is a front-bottom view of a dispenser 18 having a dispenser opening 56 in a front face 49 and a bottom face 51. Opening 56 is configured to substantially match and align with the outline of the perforation line 46 of flap 20. FIG. 15 is front-bottom view the dispenser 16 with the glove stack, box, and dispenser assembled together, and the flap removed. Opening 56 includes a hand-shaped portion on a front face 49 and extends onto end or bottom face 51. The configuration of seam 38 of the glove 12 is substantially aligned with both the opening in the box formed by removing flap 20 and dispenser opening 56. The portion of the opening 56 on end face 51 may extend fully to the back panel or partly to form a lip as illustrated. The proximal end of at least a portion of the glove stack 40 and cuff 32 of the top glove are exposed. The portion of the opening on the end face 51 may extend fully to the back face or partly to form a lip as illustrated. Thereby, the front face 49 of the dispenser, the box 16, posts 40 and sealing points 64 cooperate to secure the remnants in stack 24, and facilitate clean removal of gloves 12.

The term "substantially matches and aligns" as applied to flap 20 means that the configuration of perforation line 46 of the glove portion of the flap approximates or is slightly larger than the configuration of the glove seam 38 such that gloves can be extracted freely and without damage, while the remnant portions are restrained. Likewise, the term "substantially matches and aligns" as applied to the glove portion of opening 56 means that the peripheral margin of the glove portion of the opening 56 approximates or is slightly larger than the configuration of flap perforation line 46 and seam 38 such that the flap 20 can be removed after the box is installed in the dispenser, and the gloves can be extracted freely and without damage, while the remnant portions are restrained.

There are many and varied uses for the glove donning apparatus 10 and method of the invention, including the healthcare and food service industries. Specific applications in healthcare may include nurse's station, patient rooms, daycare centers and nursing homes. Food service applications include meal preparation at cafeterias, restaurants, fast food, and catering. Other applications include gas stations, factories and corporate settings or any other application where reducing the transmission of contaminants and infective agents is desired. The glove donning apparatus of the invention also has domestic applications such as household cleaning, infant care, pet bathing, food preparation, painting and garbage removal.

Since modifications within the spirit and scope of the invention may readily be effected by persons skilled within the art, it is to be understood that this invention is not limited to the particular embodiments described by way of example hereinabove. In the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

REFERENCE NUMBERS IN THE DRAWINGS

| | |
|---|---|
| 10 | Glove Donning Apparatus |
| 12 | Glove |
| 14 | Glove sheet |
| 15 | Box front panel |
| 16 | Box or Package |
| 17 | Box end or bottom panel |
| 18 | Dispenser |
| 20 | Flap |
| 22 | Remnant |
| 24 | Stack |
| 26 | Bottom Layer |
| 28 | Top Layer |
| 30 | Tail |
| 32 | Cuff |
| 34 | Proximal End |
| 36 | Hand Opening |
| 38 | Seam |
| 40 | Post |
| 42 | Hole |
| 44 | Back Template |
| 45 | Front Template |
| 46 | Box Perforation |
| 48 | Front Portion of dispenser |
| 49 | Dispenser Front Face |
| 50 | Rear Portion of dispenser |
| 51 | Dispenser End or Bottom Face |
| 52 | Hinge |
| 54 | Wall Mount |
| 56 | Dispenser Opening |
| 58 | Dispenser Top Opening |
| 60 | Alternative Glove Sheet |
| 62 | Tab |
| 64 | Sealing Point |

The invention claimed is:

1. An apparatus for donning hygienic gloves comprising:
a plurality of glove sheets bound together in a stack, each glove sheet comprising a bi-layered glove and a remnant portion, the glove being frangibly connected to the remnant portion;
a box containing the stack of glove sheets; and a dispenser configured to removably hold the box, the dispenser having an opening from which the gloves may be extracted;

wherein the frangible connection between the glove and remnant portion is stronger at a cuff portion than at a finger portion of the glove.

2. The apparatus of claim 1, wherein the glove is defined by a hand-shaped seal between the layers of each glove sheet.

3. The apparatus of claim 1, wherein the remnant portions of the stack are at least partially affixed to the box.

4. The apparatus of claim 1, wherein the box has a hand-shaped, detachable flap on a front panel that is substantially aligned with the gloves in the stack.

5. The apparatus of claim 1 wherein each glove sheet is rectangular and the box has a matching rectangular configuration to securely retain the remnant portions as gloves are extracted.

6. The apparatus of claim 1, wherein each glove sheet has a top layer and bottom layer, each glove sheet having a proximal end that includes the cuff portion of the glove, the bottom layer being longer than the top layer at the cuff portion, and the cuff portion including an opening configured to receive a user's hand.

7. The apparatus of claim 1, wherein the remnant portion of each glove sheet in the stack is attached to the remnant portion of at least one adjacent glove sheet in the stack, and wherein the glove of each glove sheet is unattached to adjacent gloves in the stack or is only loosely attached at the cuff portion of the glove.

8. The apparatus of claim 1, wherein the remnant portions in the stack are bound together at multiple sealing points.

9. The apparatus of claim 1, further comprising a plurality of interior posts that extend though and bind together the remnant portions of the stack of glove sheets.

10. The apparatus of claim 9, further comprising a back template connected to the posts and a front template connected to the posts, the stack of glove sheets being held between the front and back templates.

11. An apparatus for donning hygienic gloves comprising:
a plurality of glove sheets, each sheet comprising,
a top layer and bottom layer sealed together along a hand-shaped seam, the seam frangibly connecting a glove to a remnant portion of the sheet,
a proximal end of the sheet comprising a cuff of the glove,
a hand opening in the cuff, and
the bottom layer being longer than the top layer at the cuff;

wherein the plurality of glove sheets are stacked with the gloves being aligned within the stack, and the remnant portions of each sheet being bound together;

a box at least partially containing the stack of glove sheets, the box having a flap that extends between a front panel and an end panel of the box, a portion of the flap on the front panel being hand-shaped and configured to substantially match and align with the hand-shaped seam on the stack of glove sheets, the portion of the flap on the end panel being configured to align with a proximal end of the stack, the flap being detachable from the box; and a dispenser configured to removably hold the box, the dispenser having an opening that extends between a front face and an end face of the dispenser, a portion of the opening on the dispenser front face being hand-shaped and configured to substantially match and align with the hand-shaped portion of the flap on the front panel of the box, a portion of the dispenser opening on the end face of the dispenser being configured to match and align with the portion of the flap on the end panel of the box.

12. The apparatus of claim 11, wherein the remnant portions in the stack are bound together at multiple sealing points.

13. The apparatus of claim 11 wherein the frangible connection between the glove and remnant portion is stronger the cuff than at a finger portion of the glove.

14. The apparatus of claim 11 further comprising a back template held within the box, and a plurality of interior posts attached to the back template and extending though the remnant portions of the stack of glove sheets.

15. The apparatus of claim 11, wherein the dispenser is a one-piece container that has a box receiving opening.

16. An apparatus for donning hygienic gloves comprising:
a plurality of glove sheets bound together in a stack, each glove sheet comprising a bi-layered glove and a remnant portion, the glove being frangibly connected to the remnant portion;
a box containing the stack of glove sheets;
a dispenser configured to removably hold the box, the dispenser having an opening from which the gloves may be extracted;
a plurality of interior posts that extend though and bind together the remnant portions of the stack of glove sheets; and
a back template connected to the posts and a front template connected to the posts, the stack of glove sheets being held between the front and back templates.

* * * * *